US008466276B2

(12) United States Patent
Deng et al.

(10) Patent No.: US 8,466,276 B2
(45) Date of Patent: Jun. 18, 2013

(54) OLIGOMER CONJUGATES OF HETEROPENTACYCLIC NUCLEOSIDES

(75) Inventors: Bo-Liang Deng, Madison, AL (US);
Timothy A. Riley, Huntsville, AL (US);
Jennifer Riggs-Sauthier, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 195 days.

(21) Appl. No.: 12/918,780

(22) PCT Filed: Feb. 20, 2009

(86) PCT No.: PCT/US2009/001104
§ 371 (c)(1),
(2), (4) Date: Oct. 27, 2010

(87) PCT Pub. No.: WO2009/105258
PCT Pub. Date: Aug. 27, 2009

(65) Prior Publication Data
US 2011/0039797 A1    Feb. 17, 2011

Related U.S. Application Data

(60) Provisional application No. 61/066,815, filed on Feb. 22, 2008.

(51) Int. Cl.
*C07H 19/056* (2006.01)
*A01N 43/04* (2006.01)
*A61K 31/70* (2006.01)

(52) U.S. Cl.
USPC .......................................... 536/28.7; 514/43

(58) Field of Classification Search
None
See application file for complete search history.

(56) References Cited

U.S. PATENT DOCUMENTS

| 3,798,209 | A | 3/1974 | Witkowski et al. |
| 5,672,662 | A | 9/1997 | Harris et al. |
| 2003/0004119 | A1 | 1/2003 | Ganguly et al. |
| 2005/0136031 | A1 | 6/2005 | Bentley et al. |
| 2007/0072796 | A1 | 3/2007 | Phiasivongsa et al. |

FOREIGN PATENT DOCUMENTS

| EP | 1 279 405 | 1/2003 |
| WO | WO 97/04796 | 2/1997 |
| WO | WO 97/21452 | 6/1997 |
| WO | WO 02/098949 | 12/2002 |
| WO | WO 2004/048397 | 6/2004 |
| WO | WO 2004052905 A2 * | 6/2004 |
| WO | WO 2005/058367 | 6/2005 |
| WO | WO 2006/040558 | 4/2006 |
| WO | WO 2006/113615 | 10/2006 |
| WO | WO 2009/042064 | 4/2009 |

OTHER PUBLICATIONS

Chen, et al., "Synthesis and Properties of ABA Amphiphiles," J. Org. Chem., vol. 64, pp. 6870-6873, (1999).
Marumoto, et al., "Synthesis and Coronary Vasodilating Activity of 2-Substituted Adenosines," Chem. Pharm. Bull., vol. 23, No. 4, pp. 759-774, (Jan. 1, 1975).
PCT International Search Report corresponding to PCT Application No. PCT/US2009/001104 date of mailing Jun. 23, 2009.
PCT International Preliminary Report on Patentability corresponding to PCT Application No. PCT/US2009/001104 date of mailing Sep. 2, 2010.
Enzon Pharmaceuticals, Macromolecular Engineering Technologies, pp. 1-14, (2004).
Nektar™—Transforming Therapeutics, Nektar Molecule Engineering: Polyethylene Glycol and Derivatives for Advanced PEGylation, pp. 1-20, Catalog—2003, (Jul. 2003).
Nektar™—Transforming Therapeutics, Nektar Advanced PEGylation: Polyethylene Glycol and Derivatives for Advanced PEGylation, pp. 1-24, Catalog—2004, (Jul. 2004).
Nektar™—Transforming Therapeutics, Nektar Advanced PEGylation: Polyethylene Glycol and Derivatives for Advanced PEGylation, pp. 1-30, (Catalog 2005-2006).
NOF Corporation, "PEG Derivatives, Phospholipid and Drug Delivery Materials for Pharmaceuticals", pp. 1-46, Catalogue 2003—1st, (Jan. 2003).
NOF Corporation, "PEG Derivatives, Phospholipid and Drug Delivery Materials for Pharmaceuticals", pp. 1-50, Catalogue 2003—2nd, (Mar. 2004).
NOF Corporation, "PEG Derivatives, Phospholipids and Drug Delivery Materials for Pharmaceutical Products and Formulations", pp. 1-59, Catalogue Ver. 8, (Apr. 2006).
Polypure, Products; PEG amines; PEG acids and amino acids; PEG thiols and disulfides; BIOTINS, (Apr. 2004).
Polypure, Products; PEG amines; PEG acids and amino acids; PEG thiols and disulfides; BIOTINS, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™ (dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, pp. 1-49, (Catalog—Mar. 1995).
Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, pp. 1-17, (Catalog—Jul. 2001).

* cited by examiner

Primary Examiner — Layla Bland
(74) Attorney, Agent, or Firm — Timothy A. Marquart

(57) ABSTRACT

The invention provides small molecule drugs that are chemically modified by covalent attachment of a water-soluble oligomer.

13 Claims, No Drawings

OLIGOMER CONJUGATES OF HETEROPENTACYCLIC NUCLEOSIDES

CROSS REFERENCE TO RELATED APPLICATIONS

This application is a 35 U.S.C. §371 application of International Application No. PCT/US2009/001104, filed 20 Feb. 2009, designating the United States, which claims the benefit of priority under 35 U.S.C. §119(e) to U.S. Provisional Patent Application Ser. No. 61/066,815, filed 22 Feb. 2008, both of which are incorporated herein by reference in their entireties.

FIELD OF THE INVENTION

This invention comprises (among other things) chemically modified heteropentacyclic nucleosides that possess certain advantages over versions lacking the chemical modification. The chemically modified versions described herein relate to and/or have application(s) in (among others) the fields of drug discovery, pharmacotherapy, physiology, organic chemistry and polymer chemistry.

BACKGROUND OF THE INVENTION

Heteropentacyclic nucleosides (e.g., ribavirin, showdomycin and pyrazomycin) are agents having known pharmacologic activities. The heteropentacyclic nucleoside ribavirin, for example, can inhibit the replication of both RNA and DNA viruses. Showdomycin and pyrazomycin are heteropentacyclic nucleosides known to have antibiotic activity.

Some drugs in the heteropentacyclic nucleoside class are extensively metabolized via first-pass hepatic metabolism. In addition, some drugs in this class (and ribavirin in particular) can cause hemolytic anemia, a serious and often life-threatening condition. Anemia can occur when ribavirin diffuses into and accumulates within erythrocytes, due to an inability of erythrocytes to hydrolyze (dephosphorylate) the drug. Erythrocytes are unable to hydrolyze the drug because they lack phosphatases with the result that the ribavirin phosphate concentration can reach a level that is 60- to 100-fold higher than its plasma concentration. At these high levels, ribavirin phosphate can deplete intracellular ATP, impair ATP-dependent oxidative respiratory pathway, damage erythrocyte membrane integrity and eventually cause hemolytic anemia. Although these effects are reversible and may be mitigated by removing the drug, reducing the drug or administering erythropoietin, it would be advantageous to be able to administer a compound having ribavirin and other heteropentacyclic nucleosides without regard for these or other undesired effects.

The present invention seeks to address these and other needs in the art.

SUMMARY OF THE INVENTION

In one or more embodiments of the invention, a compound is provided, the compound comprising a heteropentacyclic nucleoside residue covalently attached via a stable or degradable linkage to a water-soluble, non-peptidic oligomer.

Exemplary compounds of the invention include those having the following structure:

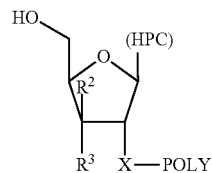

(Formula I-Ca)

wherein:

(HPC) is a five-membered heterocyclic moiety, preferably unsaturated and preferably containing from one to three nitrogen atoms, more preferably selected from the group consisting of

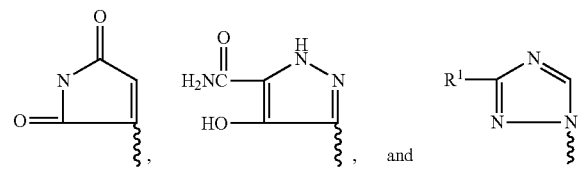

wherein $R^1$ is —C≡N, —C(O)NH$_2$, —C(S)NH$_2$, —C(O)OCH$_3$, —C(NH)NH$_2$ and —N(NH)N(H)OH;

$R^2$ is hydrogen or hydroxyl;

$R^3$ is hydroxyl when $R^2$ is hydrogen and $R^3$ is hydrogen when $R^2$ is hydroxyl;

X is a spacer moiety; and

POLY is a water-soluble, non-peptidic oligomer, and 5'-phosphates and 3',5'-cyclic phosphates thereof and ammonium and alkali metal salts of each of the 5'-phosphates and 3',5'-cyclic phosphates.

Additional exemplary compounds of the invention include those having the following structure:

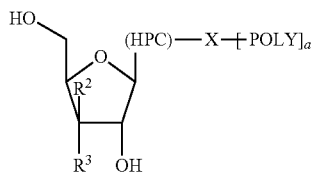

(Formula I-Cb)

wherein:

(HPC)-X-[POLY]$_a$ is a five-membered heterocyclic moiety, preferably unsaturated and preferably containing from one to three nitrogen atoms to which attached is one (when a=1) or two (when a=2) POLY species (each POLY being a water-soluble, non-peptidic oligomer), through X, a spacer moiety, $R^2$ is hydrogen or hydroxyl; and $R^3$ is hydroxyl when $R^2$ is hydrogen and $R^3$ is hydrogen when $R^2$ is hydroxyl; and 5'-phosphates and 3',5'-cyclic phosphates thereof and ammonium and alkali metal salts of each of the 5'-phosphates and 3',5'-cyclic phosphates. Preferably, prior to any attachment of a water-soluble, non-peptidic oligomer through the spacer moiety, the five-membered ring is preferably selected from the group consisting of

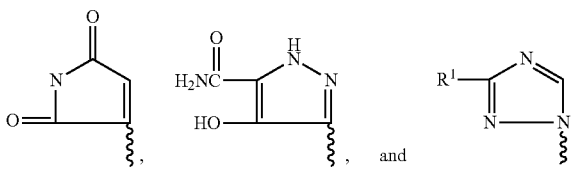

wherein $R^1$ is —C≡N, —C(O)NH$_2$, —C(S)NH$_2$, —C(O)OCH$_3$, —C(NH)NH$_2$ and —N(NH)N(H)OH.

Further exemplary compounds of the invention include those having the following structure:

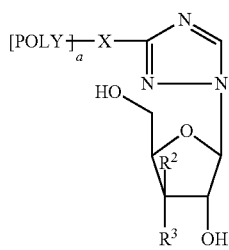

(Formula I-Cc)

wherein:
$R^2$ is hydrogen or hydroxyl;
$R^3$ is hydroxyl when $R^2$ is hydrogen and $R^3$ is hydrogen when $R^2$ is hydroxyl;
X is a spacer moiety;
each POLY is independently a water-soluble, non-peptidic oligomer;
and (a) is one or two,
and 5'-phosphates and 3',5'-cyclic phosphates thereof and ammonium and alkali metal salts of each of the 5'-phosphates and 3',5'-cyclic phosphates.

Further exemplary compounds of the invention include those having the following structure:

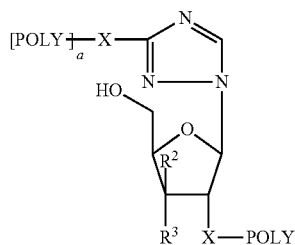

(Formula I-Cd)

wherein:
$R^2$ is hydrogen or hydroxyl;
$R^3$ is hydroxyl when $R^2$ is hydrogen and $R^3$ is hydrogen when $R^2$ is hydroxyl;
each X is independently a spacer moiety;
each POLY is independently a water-soluble, non-peptidic oligomer;
and (a) is one or two,
and 5'-phosphates and 3',5'-cyclic phosphates thereof and ammonium and alkali metal salts of each of the 5'-phosphates and 3',5'-cyclic phosphates.

A "heteropentacyclic nucleoside residue" (or a "residue of a heteropentacyclic nucleoside") is a compound having a structure of a heteropentacyclic nucleoside that is altered by the presence of one or more bonds, which bonds serve to attach (either directly or indirectly) one or more water-soluble, non-peptidic oligomers. In this regard, any heteropentacyclic nucleoside have pharmacologic activity can be used. Exemplary heteropentacyclic nucleosides have a structure encompassed by the structure defined herein as Formula I, as follows:

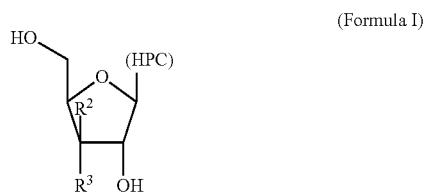

(Formula I)

wherein:
(HPC) is a five-membered heterocyclic moiety, preferably unsaturated and preferably containing from one to three nitrogen atoms, more preferably selected from the group consisting of

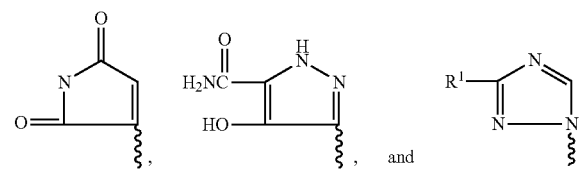

wherein $R^1$ is —C≡N, —C(O)NH$_2$, —C(S)NH$_2$, —C(O)OCH$_3$, —C(NH)NH$_2$ and —N(NH)N(H)OH;
$R^2$ is hydrogen or hydroxyl; and
$R^3$ is hydroxyl when $R^2$ is hydrogen and $R^3$ is hydrogen when $R^2$ is hydroxyl.

In one or more embodiments of the invention, a composition is provided, the composition comprising a compound comprising a residue of a heteropentacyclic nucleoside covalently attached via a stable or degradable linkage to a water-soluble, non-peptidic oligomer, and optionally, a pharmaceutically acceptable excipient.

In one or more embodiments of the invention, a dosage form is provided, the dosage form comprising a compound comprising a residue of a heteropentacyclic nucleoside covalently attached via a stable or degradable linkage to a water-soluble, non-peptidic oligomer, wherein the compound is present in a dosage form.

In one or more embodiments of the invention, a method is provided, the method comprising covalently attaching a water-soluble, non-peptidic oligomer to a heteropentacyclic nucleoside.

In one or more embodiments of the invention, a method is provided, the method comprising administering a compound comprising a residue of a heteropentacyclic nucleoside covalently attached via a stable or degradable linkage to a water-soluble, non-peptidic oligomer.

These and other objects, aspects, embodiments and features of the invention will become more fully apparent to one of ordinary skill in the art when read in conjunction with the following detailed description.

DETAILED DESCRIPTION OF THE INVENTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention may comprise the following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like.

"Branched," in reference to the geometry or overall structure of an oligomer, refers to an oligomer having two or more polymer "arms" extending from a branch point.

"Forked," in reference to the geometry or overall structure of an oligomer, refers to an oligomer having two or more functional groups (through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, thiolesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single (i.e., the same) molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the corticosteroid residue. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the corticosteroid residue. A composition comprised of bimodal conjugates may, however, include one or more nonconjugate substances such as solvents, reagents, excipients, and so forth A "heteropentacyclic nucleoside" refers to an organic, inorganic, or organometallic compound having a molecular weight of less than about 1000 Daltons (and typically less than 500 Daltons) and having some pharmacological activity, such as antiviral and/or antibiotic activity.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

A "reduced rate of metabolism" refers to a measurable reduction in the rate of metabolism of a water-soluble oligomer-small molecule drug conjugate as compared to the rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and may pass through the liver prior to reaching the systemic circulation. Because the liver is the primary site of drug metabolism or biotransformation, a substantial amount of drug may be metabolized before it reaches the systemic circulation. The degree of first pass metabolism, and thus, any reduction thereof, may be measured by a number of different approaches. For instance, animal blood samples may be collected at timed intervals and the plasma or serum analyzed by liquid chromatography/mass spectrometry for metabolite levels. Other techniques for measuring a "reduced rate of metabolism" associated with the first pass metabolism and other metabolic processes are known, described herein and/or in the relevant literature, and/or can be determined by one of ordinary skill in the art. Preferably, a conjugate of the invention can provide a reduced rate of metabolism reduction satisfying at least one of the following values: at least about 5%; at least about 15%; at least about 20%; at least about 25%; at least about 30%; at least about 40%; at least about 60%, at least about 70%, at least about 80%, and at least about 90%.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to component that may be included in the compositions of the invention and that causes no significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

For simplicity, chemical moieties are defined and referred to throughout primarily as univalent chemical moieties (e.g., alkyl, aryl, etc.), divalent moieties (e.g., a spacer moiety providing a "bridge" between two moieties), or polyvalent moieties (e.g., a spacer moiety providing a "bridge" between three or more moieties). For any given moiety, one of ordinary skill in the art will be able to understand the required valence based on the chemical structures provided herein. For moieties that are individual atoms, all atoms are understood to have their normal number of valences for bond formation (i.e., 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homobifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein.

"Optional" or "optionally" means that the subsequently described circumstance may but need not necessarily occur, so that the description includes instances where the circumstance occurs and instances where it does not.

As indicated above, the present invention is directed to (among other things) a compound comprising a residue of heteropentacyclic nucleoside covalently attached via a stable or degradable linkage to a water-soluble, non-peptidic oligomer.

In one or more embodiments of the invention, a compound is provided, the compound comprising a residue of heteropentacyclic nucleoside covalently attached via a stable or degradable linkage to a water-soluble, non-peptidic oligomer, wherein the heteropentacyclic nucleoside has a structure encompassed by the following formula:

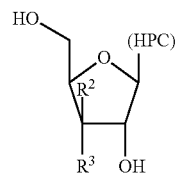

(Formula I)

wherein:

(HPC) is a five-membered heterocyclic moiety, preferably unsaturated and preferably containing from one to three nitrogen atoms, more preferably selected from the group consisting of

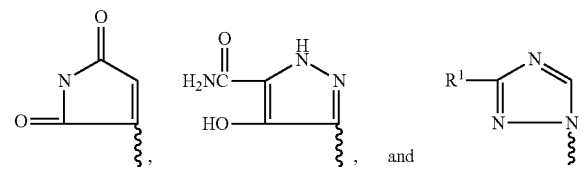

wherein $R^1$ is —C≡N, —C(O)$NH_2$, —C(S)$NH_2$, —C(O)$OCH_3$, —C(NH)$NH_2$ and —N(NH)N(H)OH;

$R^2$ is hydrogen or hydroxyl; and $R^3$ is hydroxyl when $R^2$ is hydrogen and $R^3$ is hydrogen when $R^2$ is hydroxyl.

The small molecule to which the water-soluble, nonpeptidic oligomer is attached can be a heteropentacyclic nucleoside. Specific examples of which include ribavirin, showdomycin, and pyrazomycin.

It is believed that an advantage of the compounds of the present invention is their ability to retain some degree of pharmacologic activity while also exhibiting a decrease in side effects upon administration to a patient. Although not wishing to be bound by theory, it is believed that the oligomer-containing compounds described herein—in contrast to the oligomer-free "original" heteropentacyclic nucleoside—are not metabolized as readily because the oligomer serves to reduce the overall affinity of the compound to substrates that can metabolize heterocyclic nucleosides. Further, it is believed that the compounds of the present invention have reduced uptake and subsequent accumulation in erythrocytes as compared to the oligomer-free version of the heteropentacyclic nucleoside. Even should the linkage between the residue of the heteropentacyclic nucleoside and the oligomer be releasable, the compound still offers advantages (such as avoiding first-pass metabolism upon initial absorption).

As indicated above, the compounds of the invention include a residue of a heteropentacyclic nucleoside. Assays for determining whether a given compound (regardless of whether the compound includes a water-soluble, non-peptidic oligomer or not) has activity are described herein and/or are otherwise known to those of ordinary skill in the art.

Exemplary heteropentacyclic nucleosides are encompassed by the following formula:

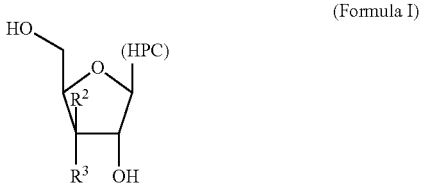

(Formula I)

wherein:

(HPC) is a five-membered heterocyclic moiety, preferably unsaturated and preferably containing from one to three nitrogen atoms, more preferably selected from the group consisting of

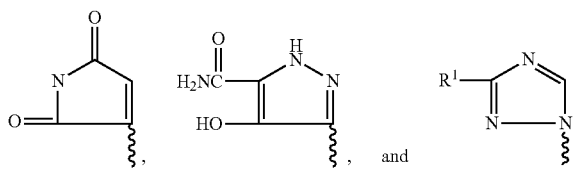

wherein $R^1$ is —C≡N, —C(O)NH$_2$, —C(S)NH$_2$, —C(O)OCH$_3$, —C(NH)NH$_2$ and —N(NH)N(H)OH;

$R^2$ is hydrogen or hydroxyl; and $R^3$ is hydroxyl when $R^2$ is hydrogen and $R^3$ is hydrogen when $R^2$ is hydroxyl.

In one or more embodiments, the heteropentacyclic nucleoside is encompassed by the following structure:

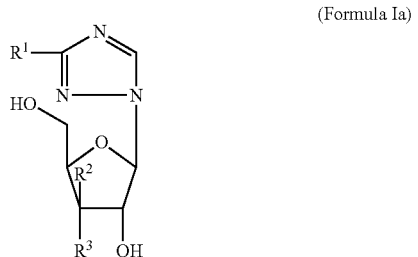

(Formula Ia)

wherein: $R^1$ is —C≡N, —C(O)NH$_2$, —C(S)NH$_2$, —C(O)OCH$_3$, —C(NH)NH$_2$ and —N(NH)N(H)OH; $R^2$ is hydrogen or hydroxyl; and $R^3$ is hydroxyl when $R^2$ is hydrogen and $R^3$ is hydrogen when $R^2$ is hydroxyl. In one or more embodiments, the small molecule is ribavirin, which has the following structure:

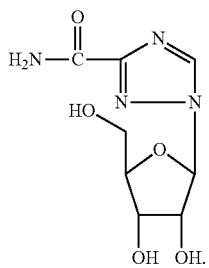 [SMILES: NC(=O)c1ncn(C2OC(CO)C(O)C2O)n1]

Compounds encompassed by Formula Ia are described in U.S. Pat. No. 3,798,209 and can be prepared according to known methods.

In some instances, heteropentacyclic nucleosides can be obtained from commercial sources. In addition, heteropentacyclic nucleosides can be obtained through chemical synthesis. Examples of heteropentacyclic nucleosides as well as synthetic approaches for preparing the same are described in the literature and in, for example, U.S. Pat. No. 3,798,209.

Each of these (and other) heteropentacyclic nucleosides can be covalently attached (either directly or through one or more atoms) to a water-soluble, non-peptidic oligomer.

Small molecule drugs useful in the invention generally have a molecular weight of less than 1000 Da. Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

Heteropentacyclic nucleosides for coupling to a water-soluble, non-peptidic oligomer possesses a free hydroxyl, carboxyl, thio, amino group, or the like (i.e., "handle") suitable for covalent attachment to the oligomer. In addition, a heteropentacyclic nucleoside can be modified by introduction of a reactive group, preferably by conversion of one of its existing functional groups to a functional group suitable for formation of a stable covalent linkage between the oligomer and the drug. Both approaches are illustrated in the Experimental section.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, the water-soluble, non-peptidic oligomer it can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble, non-peptidic polymer includes $CH_3-(OCH_2CH_2)_n-$, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the heteropentacyclic nucleoside (in contrast to the stepwise addition of one or more monomers to effectively "grow" the oligomer onto the heteropentacyclic nucleoside), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut," to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble, non-peptidic polymer is attached to the heteropentacyclic nucleoside) may be a single bond, a single atom, such as an oxygen atom or a sulfur atom, two atoms, or a number of atoms. A spacer moiety is typically but is not necessarily linear in nature. The spacer moiety, "X," is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety of the invention, X, may be any of the following: "—" (i.e., a covalent bond, that may be stable or degradable, between the heteropentacyclic nucleoside and the water-soluble, non-peptidic oligomer), —C(NH)NH$_2$—, —NH$_2$C(NH)—, —O—, —NH—, —S—, —C(O)—, C(O)—NH, NH—C(O)—NH, —O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—, —CH$_2$—CH$_2$—C(O)—CH$_2$—CH$_2$—, —CH$_2$—CH$_2$—C(O)—, —CH$_2$—CH$_2$—C(O)—NH—CH$_2$—CH$_2$—NH—, —CH$_2$—CH$_2$—C(O)—NH—CH$_2$—CH$_2$—NH—C(O)—, —CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or nascent oligomer when it is desired to "grow" the oligomer onto the heteropentacyclic nucleoside) with a corresponding functional group within the heteropentacyclic nucleoside. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) group on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde group is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4.

Optionally, the terminus of the water-soluble, non-peptidic oligomer not bearing a functional group is capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the heteropentacyclic nucleoside may not have a functional group suited for conjugation. In this instance, it is possible to modify (or "functionalize") the "original" heteropentacyclic nucleoside so that it does have a functional group suited for conjugation. For example, if the heteropentacyclic nucleoside has an amide group, but an amine group is desired; it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of a heteropentacyclic nucleoside bearing a carboxyl group wherein the carboxyl group-bearing small molecule heteropentacyclic nucleoside is coupled to an amino-terminated oligomeric ethylene glycol, to provide a conjugate having an amide group covalently linking the heteropentacyclic nucleoside to the oligomer. This can be performed, for example, by combining the carboxyl group-bearing small molecule agent with the amino-terminated oligomeric ethylene glycol in the presence of a coupling reagent, (such as dicyclohexylcarbodiimide or "DCC") in an anhydrous organic solvent.

Further, it is possible to prepare a conjugate of a heteropentacyclic nucleoside bearing a hydroxyl group wherein the hydroxyl group-bearing heteropentacyclic nucleoside is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a heteropentacyclic nucleoside bearing a ketone group by first reducing the ketone group to form the corresponding hydroxyl group. Thereafter, the heteropentacyclic nucleoside now bearing a hydroxyl group can be coupled as described herein.

In still another instance, it is possible to prepare a conjugate of a heteropentacyclic nucleoside bearing an amine group. In one approach, the amine group-bearing small molecule compound and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule of interest and the carbonyl carbon of the aldehyde-bearing oligomer.

In another approach for preparing a conjugate of a heteropentacyclic nucleoside bearing an amine group, a carboxylic acid-bearing oligomer and the amine group-bearing small molecule of interest are combined, typically in the presence of a coupling reagent (e.g., DCC). The result is an amide linkage formed between the amine group of the amine group-containing small molecule and the carbonyl of interest the carboxylic acid-bearing oligomer.

Exemplary compounds of the invention include those having the following structure:

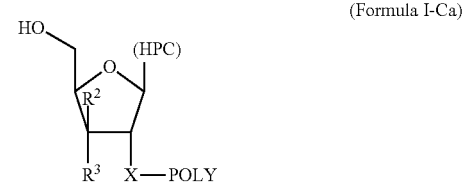

(Formula I-Ca)

wherein:

(HPC) is a five-membered heterocyclic moiety, preferably unsaturated and preferably containing from one to three nitrogen atoms, more preferably selected from the group consisting of

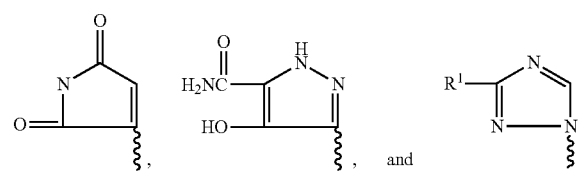

wherein R' is —C≡N, —C(O)NH$_2$, —C(S)NH$_2$, —C(O)OCH$_3$, —C(NH)NH$_2$ and —N(NH)N(H)OH;

R$^2$ is hydrogen or hydroxyl;

R$^3$ is hydroxyl when R$^2$ is hydrogen and R$^3$ is hydrogen when R$^2$ is hydroxyl;

X is a spacer moiety; and

POLY is a water-soluble, non-peptidic oligomer, and 5'-phosphates and 3',5'-cyclic phosphates thereof and ammonium and alkali metal salts of each of the 5'-phosphates and 3',5'-cyclic phosphates.

Additional exemplary compounds of the invention include those having the following structure:

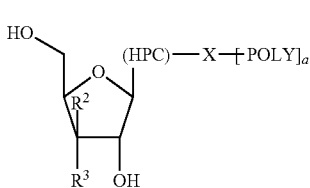
(Formula I-Cb)

wherein:

(HPC)-X-[POLY], is a five-membered heterocyclic moiety, preferably unsaturated and preferably containing from one to three nitrogen atoms to which attached is one (when a=1) or two (when a=2) POLY species (each POLY being a water-soluble, non-peptidic oligomer), through X, a spacer moiety, $R^2$ is hydrogen or hydroxyl; and $R^3$ is hydroxyl when $R^2$ is hydrogen and $R^3$ is hydrogen when $R^2$ is hydroxyl; and 5'-phosphates and 3',5'-cyclic phosphates thereof and ammonium and alkali metal salts of each of the 5'-phosphates and 3',5'-cyclic phosphates. Preferably, prior to any attachment of a water-soluble, non-peptidic oligomer through the spacer moiety, the five-membered ring is preferably selected from the group consisting of

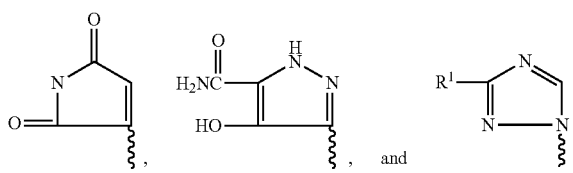

wherein $R^1$ is —C≡N, —C(O)NH$_2$, —C(S)NH$_2$, —C(O)OCH$_3$, —C(NH)NH$_2$ and —N(NH)N(H)OH.

Further exemplary compounds of the invention include those having the following structure:

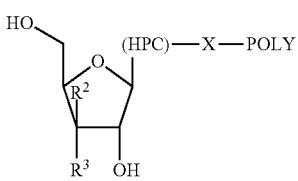
(Formula I-Cb.1)

wherein:

(HPC)-X-POLY is a five-membered heterocyclic moiety, preferably unsaturated and preferably containing from one to three nitrogen atoms to which is attached a POLY, water-soluble, non-peptidic oligomer, through X, a spacer moiety, $R^2$ is hydrogen or hydroxyl; and $R^3$ is hydroxyl when $R^2$ is hydrogen and $R^3$ is hydrogen when $R^2$ is hydroxyl; and 5'-phosphates and 3',5'-cyclic phosphates thereof and ammonium and alkali metal salts of each of the 5'-phosphates and 3',5'-cyclic phosphates. Preferably, prior to any attachment of a water-soluble, non-peptidic oligomer through the spacer moiety, the five-membered ring is preferably selected from the group consisting of

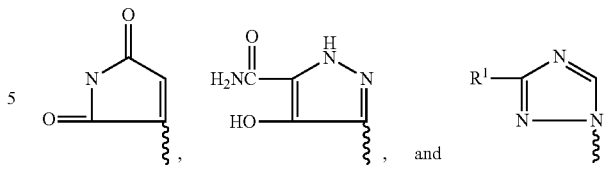

wherein R' is —C≡N, —C(O)NH$_2$, —C(S)NH$_2$, —C(O)OCH$_3$, —C(NH)NH$_2$ and —N(NH)N(H)OH.

Further exemplary compounds of the invention include those having the following structure:

(Formula I-Cc)

wherein:

$R^2$ is hydrogen or hydroxyl;

$R^3$ is hydroxyl when $R^2$ is hydrogen and $R^3$ is hydrogen when $R^2$ is hydroxyl;

X is a spacer moiety;

each POLY is independently a water-soluble, non-peptidic oligomer;

and (a) is one or two, and 5'-phosphates and 3',5'-cyclic phosphates thereof and ammonium and alkali metal salts of each of the 5'-phosphates and 3',5'-cyclic phosphates.

Further additional exemplary compounds of the invention include those having the following structure:

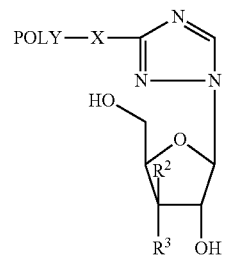
(Formula I-Cc.1)

wherein:

$R^2$ is hydrogen or hydroxyl;

$R^3$ is hydroxyl when $R^2$ is hydrogen and $R^3$ is hydrogen when $R^2$ is hydroxyl;

X is a spacer moiety; and

POLY is a water-soluble, non-peptidic oligomer, and 5'-phosphates and 3',5'-cyclic phosphates thereof and ammonium and alkali metal salts of each of the 5'-phosphates and 3',5'-cyclic phosphates.

Further exemplary compounds of the invention include those having the following structure:

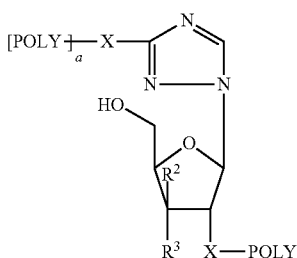

(Formula I-Cd)

wherein:

$R^2$ is hydrogen or hydroxyl;

$R^3$ is hydroxyl when $R^2$ is hydrogen and $R^3$ is hydrogen when $R^2$ is hydroxyl;

each X is independently a spacer moiety;

each POLY is independently a water-soluble, non-peptidic oligomer;

and (a) is one or two, and 5'-phosphates and 3',5'-cyclic phosphates thereof and ammonium and alkali metal salts of each of the 5'-phosphates and 3',5'-cyclic phosphates.

Further exemplary compounds of the invention include those having the following structure:

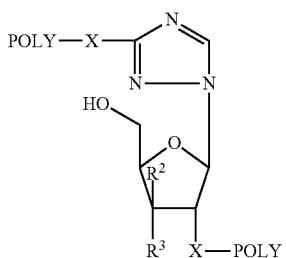

(Formula I-Cd.1)

wherein:

$R^2$ is hydrogen or hydroxyl;

$R^3$ is hydroxyl when $R^2$ is hydrogen and $R^3$ is hydrogen when $R^2$ is hydroxyl;

each X is independently a spacer moiety; and each POLY is independently a water-soluble, non-peptidic oligomer, and 5'-phosphates and 3',5'-cyclic phosphates thereof and ammonium and alkali metal salts of each of the 5'-phosphates and 3',5'-cyclic phosphates.

With respect to identifying the optimally sized oligomer for a given compound, the following process can be followed.

First, an oligomer obtained from a monodisperse or bimodal water-soluble oligomer is conjugated to the small molecule drug. Preferably, the drug and the conjugate is orally bioavailable. Next, the metabolism of the drug bearing a water-soluble oligomer is determined using an appropriate model and compared to that of the drug lacking the water-soluble oligomer. If the results are favorable, that is to say, if, for example, the rate of metabolism is reduced in the drug bearing the water-soluble oligomer, the above steps are repeated one or more times using oligomers of the same monomer type but having a different number of subunits and the results compared. By making incremental changes in oligomer size and utilizing an experimental design approach, one can effectively identify a size of water-soluble oligomer that has an optimal reduction of metabolism when present in the drug bearing that size oligomer.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the heteropentacyclic nucleoside itself or the conjugate of a heteropentacyclic nucleoside has activity, it is possible to test such a compound. One having ordinary skill in the art using, for example, the approach followed in Example 2 can determine such activity.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that a reduction in first pass metabolism may be achieved relative to the parent drug. Such a result is advantageous for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. Preferred reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

Although useful in reducing many types of metabolism (including both Phase I and Phase II metabolism) can be reduced, the conjugates are particularly useful when the small molecule drug is metabolized by a hepatic enzyme (e.g., one or more of the cytochrome P450 isoforms) and/or by one or more intestinal enzymes.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

All ¹H NMR (nuclear magnetic resonance) data was generated by NMR spectrometer manufactured by Bruker. A list of certain compounds as well as the source of the compounds is provided below.

Example 1

Exemplary PEG-Heteropentacyclic Nucleoside Conjugates

The structures of exemplary compounds of the present invention are provided below:

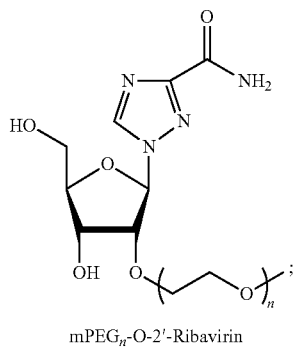

mPEG$_n$-O-2'-Ribavirin

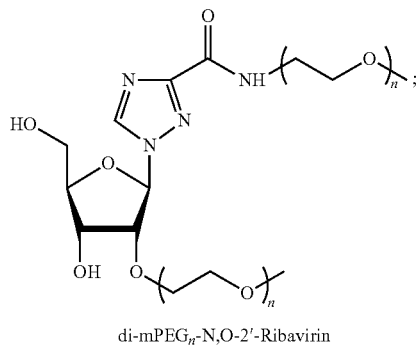

di-mPEG$_n$-N,O-2'-Ribavirin

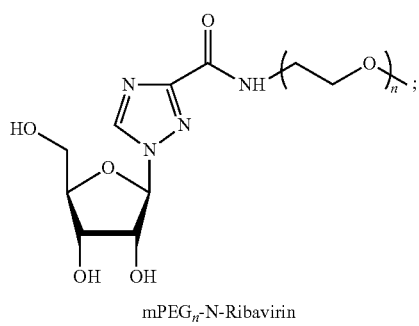

mPEG$_n$-N-Ribavirin

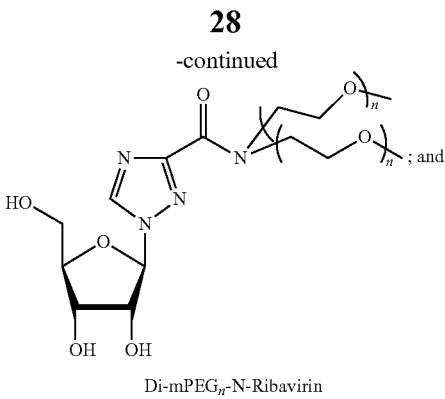

Di-mPEG$_n$-N-Ribavirin

[structure]

mPEG$_n$-N-Ribamidine wherein each appearance of (n) is independently a variable from between about 1 and about 30 (inclusive).

For the compounds prepared in this example, the following materials were used. Ribavirin was obtained from Yuhan Corporation, plant 678-1, Sungkok-Dong, Ansan-Shi Kyunggi-Do, Korea. 2,2-Dimethoxypropane was obtained from Aldrich, 98%, Lot No. 06808PD (St. Louis, Mo.). P-Toluenesulfonic acid monohydrate was obtained from Aldrich, 98.5%, Lot No. 07204EC (St. Louis, Mo.). tert-Butyldimethylsilyl chloride was obtained from Aldrich, 97%, Batch #: 12009DC (St. Louis, Mo.). tert-butylchlorodiphenylsilane was obtained from Aldrich, 98%, Batch #: 21017HB (St. Louis, Mo.). Imidazole was obtained from Aldrich, 99%, Batch #: 11721TD (St. Louis, Mo.). Pyridine was obtained from Aldrich, Batch #: 03859ED (St. Louis, Mo.). Phosphorus oxychloride was obtained from Aldrich, 99%, Batch #: 16817BD (St. Louis, Mo.). Triethylamine was obtained from Aldrich, 99.5%, Batch #: 04623HD (St. Louis, Mo.). Sodium methoxide (25 wt % solution in methanol) was obtained from Aldrich, Lot No. 08730JR (St. Louis, Mo.). 1,3-Dichloro-1,1,3,3-tetraisopropyldisiloxane was obtained from Aldrich, 97%, Lot No. 0615JD (St. Louis, Mo.). Dimethylaminopyridine was obtained from Fluka, 98%. Sodium hydride (60% dispersion in mineral oil) was obtained from Aldrich, Batch #10429PD (St. Louis, Mo.).

Examples 1A and 1B

Preparation of mPEG$_n$-O-2'-ribavirin and di-mPEG$_n$-N, O-2'-ribavirin

An exemplary synthetic scheme to prepare mPEG-O-2'-ribavirin and di-mPEGn-N, O-2'-ribavirin is schematically shown below.

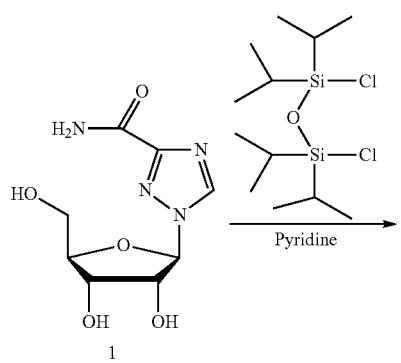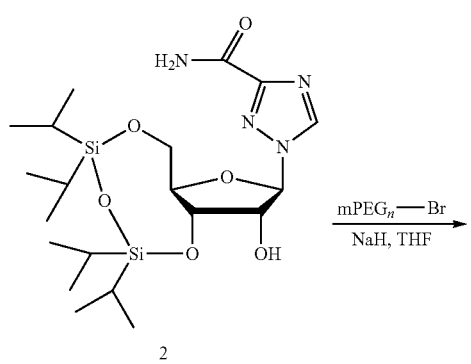

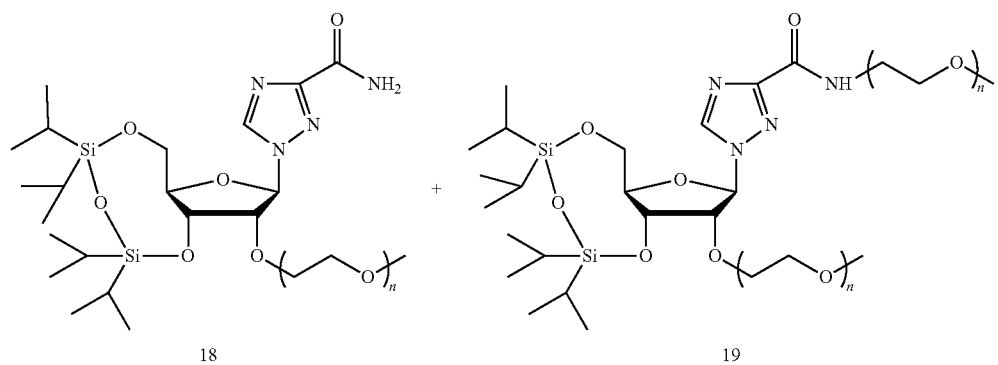

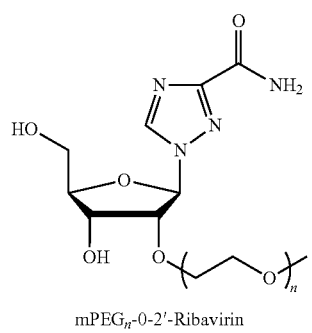

mPEG$_n$-O-2'-Ribavirin

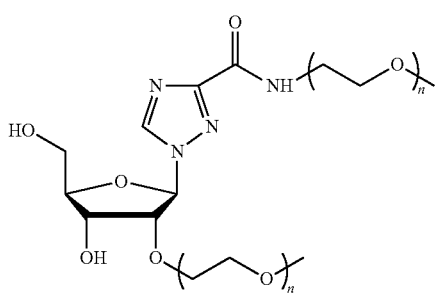

Di-mPEG$_n$-N, O-2'-Ribavirin

Synthesis of 3,5-O-(1,1,3,3-tetraisopropyl-1,3-disiloxanyl)-ribavirin 2

Ribavirin 1 (203.4 mg, 0.83 mmol) was mixed with pyridine (3.0 mL) at room temperature, and then 1,3-dichloro-1,1,3,3-tetraisopropyldisiloxane (0.33 mL, 1.00 mmol) was added. The resulting mixture was stirred at room temperature for 23.5 hours. Water was added to quench the reaction and extracted with EtOAc (3×20 mL). The combined organic solution was washed with brine (50 mL), dried over sodium sulfate, concentrated. The residue was purified by flash column chromatography on silica gel using MeOH/DCM (0-5%) to afford the product (369 mg, 91%). $^1$H-NMR (CDCl$_3$) δ8.36 (s, 1H, C$_5$H), 6.90 (bs, 1H, NH$_2$), 5.90 (s, 1H, C$_1$, H), 5.58 (bs, 1H, NH$_2$), 4.66-4.61 (m, 1H), 4.45 (d, 1H), 4.17-3.97 (m, 3H), 2.93 (s, 1H), 1.00-0.98 (m, 28H). LC-Ms: 487.3 MH$^+$.

Synthesis of Compound 18 and Compound 19

NaH (in a dispersion in mineral oil) is added to a stirred solution of compound 2 in anhydrous THF at room temperature. Thereafter, mPEG$_n$-LV [wherein LV is a leaving group, such as a halogen (e.g., bromo and chloro) or sulfonate ester (e.g., mesylate) and n is an integer from 1 to 30] is added. A mixture is formed and is subsequently stirred at room temperature for one day. Thereafter, the solvent is removed under high vacuum. The resulting residue is mixed with a mixture of EtOAc/water. The organic phase is then separated and the aqueous phase is extracted with EtOAc (2×20 mL). The combined organic solutions are then washed with brine (50 mL), dried over sodium sulfate, concentrated to afford a residue. The residue is separated by using conventional techniques to result in compound 18 and compound 19.

Synthesis of mPEG$_n$-O-2'-Ribavirin

Compound 18 is added to THF to which tetra-n-butylammonium fluoride ("TBAF") is added. The resulting mixture is stirred at room temperature. The solvent is removed and mPEG$_n$-O-2'-Ribavirin is recovered using conventional techniques.

Synthesis of Di-mPEG$_n$-N,O-2'-Ribavirin

Compound 19 is added to THF to which tetra-n-butylammonium fluoride ("TBAF") is added. The resulting mixture is stirred at room temperature. The solvent is removed and Di-mPEG$_n$-N,O-2'-Ribavirin is recovered using conventional techniques.

Example 1C

Preparation of mPEG$_n$-N-ribavirin

An exemplary synthetic scheme to prepare mPEG$_n$-N-Ribavirin is schematically shown below.

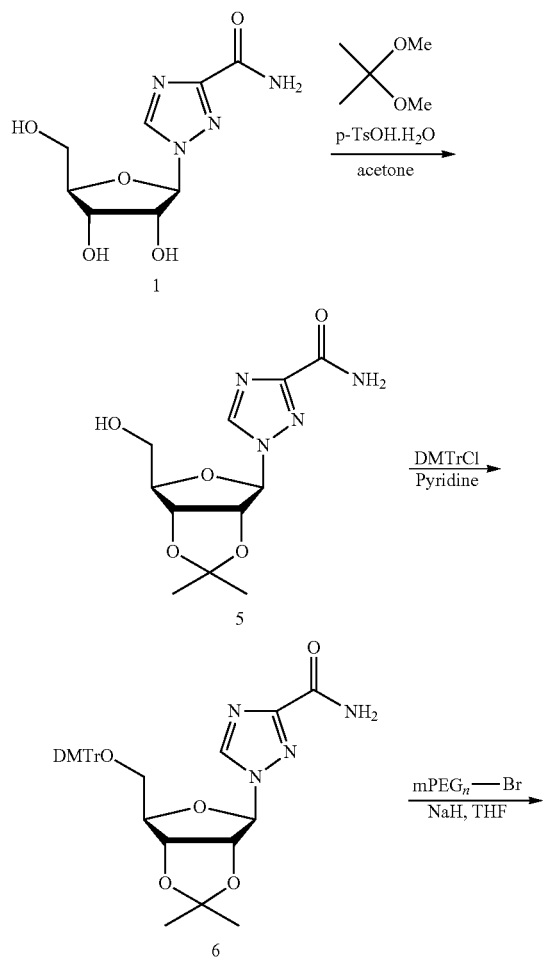

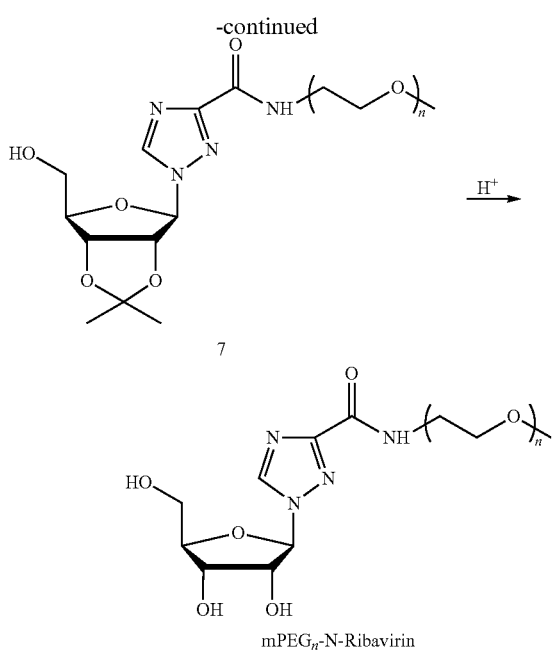

wherein (n) is a variable from between about 1 and about 30 (inclusive).

Synthesis of 1-(2',3'-Di-O-isopropylidene-β-D-ribofuranosyl)-1,2,4-triazole-3-carboxamide 5

A suspension of ribavirin 1 (318 mg, 1.302 mmol) and p-toluenesulfonic acid monohydrate ("p-TsOH") (41 mg, 0.212 mmol) was cooled to 0° C. in an ice-water bath. 2,2-Dimethoxypropane (0.18 mL, 1.438 mmol) was added. The suspension was stirred at 0° C. for 30 minutes, and then at room temperature for three hours. The mixture was still suspension. Then more of acetone (5 mL) and 2,2-dimethoxypropane (0.4 mL) was added. The mixture was stirred at room temperature for 21 hours, and then heated at 60° C. for one hour. The solution became clear. When the mixture was cooled to room temperature, 5% aqueous sodium bicarbonate (about 1 mL) was added to quench the reaction. Some precipitate was observed. The mixture was filtered and washed with acetone. The precipitate was dried under high vacuum and checked by $^1$H-NMR in DMSO. No peaks of interest were observed. The solution was concentrated under reduced and the residue was purified by column chromatography on SiO$_2$ using acetone/DCM (15%) and MeOH/acetone/DCM (Feb. 15, 1983) to afford white solid as the product (305 mg, 82%).

Run 2, a suspension of ribavirin (1.05 g, 4.3 mmol), p-toluenesulfonic acid monohydrate ("p-TsOH") (138 mg, 0.71 mmol) and 2,2-dimethoxypropane (1.0 mL, 7.99 mmol) in acetone (15 mL) was heated at 60° C. for three hours. The mixture was cooled to room temperature, and then 5% aqueous sodium bicarbonate (1 mL) was added to quench the reaction mixture. The precipitate was removed and the filtrate was collected and concentrated. The residue was purified by flash column chromatography on silica using MeOH/DCM (0-10%) to afford the product (1.21 g, 99% yield) as a white solid.

Run 3, a suspension of ribavirin (4.15 g, 17.01 mmol), p-toluenesulfonic acid monohydrate ("p-TsOH") (535 mg, 2.77 mmol) and 2,2-dimethoxypropane (3.4 mL, 27.16 mmol) in acetone (50 mL) was heated at 60° C. for four hours.

The mixture was cooled to room temperature, and then 5% aqueous sodium bicarbonate (2 mL) was added to quench the reaction mixture. The mixture was concentrated and the residue was dried under high vacuum. The residue was purified with biotage SP™ flash purification system on silica using MeOH/DCM (0-10%) to afford the product (3.91 g, 81% yield) as a white solid.

$^1$H-NMR (DMSO-d$_6$), δ8.78 (s, 1H), triazole ring proton), 7.84, 7.64 (2s, 2H, CONH$_2$), 6.20 (d, J=1.5 Hz, 1H, C$_1$H), 5.18 (dd, J=1.5 Hz, J=6.0 Hz, 1H, C$_2$, H), 4.90 (dd, J=1.8 Hz, J=6.0 Hz, 1H, C$_3$, H), 4.23 (dt, J=1.8 Hz, J=6.0 Hz, 1H, C$_4$, H), 3.51-3.35 (m, 2H, C$_5$, H), 1.50, 1.32 (2s, 6H, isopropylidene methyls). LC-Ms, 285.1 (MH$^+$).

Synthesis of 1-[5'-O-(4,4'-Dimethoxytrityl)-2',3'-di-O-isopropylidene-β-D-ribofuranosyl]-1,2,4-triazole-3-carboxamide 6

4,4'-Dimethoxytrityl chloride (156 mg, 0.44 mmol) was added to a stirred solution of 1-(2',3'-di-O-isopropylidene-β-D-ribofuranosyl)-1,2,4-triazole-3-carboxamide (compound 5) (111 mg, 0.39 mmol) in pyridine (3 mL). The resulting mixture was stirred at room temperature for 22 hours. More of 4,4'-dimethoxytrityl chloride (71 mg) was added. After 7.5 hours at room temperature, DMAP (56 mg) was added. The mixture was stirred at room temperature for another 21 hours. MeOH (2 mL) was added to quench the reaction, diluted with water, extracted with EtOAc (3×20 mL). The organic solution was washed with brine, dried over Na$_2$SO$_4$, concentrated. The residue was purified by flash column chromatography on silica gel using EtOAc/hexane (0-100%) to afford the product compound 6 (172 mg, 75% yield). $^1$H-NMR (CDCl$_3$), δ8.20 (s, 1H, C$_5$H, triazole proton), 7.30-7.11 (m, 9H, Ar—H), 6.76-6.72 (m, 4H, Ar—H), 6.86, 6.50 (2 bs, 2H, NH$_2$), 6.00 (d, J=0.9 Hz, 1H, C$_1$, H), 5.33 (dd, J=0.9-1.2 Hz, J=6.0 Hz, 1H), 4.78 (dd, J=2.1 Hz, J=6.0 Hz, 1H), 4.54 (dt, J=1.5-1.8 Hz, J=5.7 Hz, 1H), 3.72 (s, 6H, 2 CH$_3$), 3.21-3.12 (m, 2H), 1.55, 1.32 (2s, 6H, 2 CH$_3$).

Synthesis of 1-[5'-O-(4,4'-Dimethoxytrityl)-2',3'-di-O-isopropylidene-β-D-ribofuranosyl]-N-mPEG$_3$-1,2,4-triazole-3-carboxamide 7 (n=3)

NaH (60% dispersion in mineral oil, 50 mg, 1.25 mmol) was added to a stirred solution of 1-[5'-O-(4,4'-dimethoxytrityl)-2',3'-di-O-isopropylidene-β-D-ribofuranosyl]-1,2,4-triazole-3-carboxamide (compound 6) (153 mg, 0.26 mmol) in anhydrous THF (2 mL) at room temperature. Thereafter, mPEG$_3$-Br (135 mg, 0.59 mmol) was added. The resulting mixture was stirred at room temperature for 24.5 hours. The solvent was removed under high vacuum. The residue was mixed with a mixture of EtOAc/water (40 mL, 50%). The organic phase was separated and the aqueous phase was extracted with EtOAc (2×20 mL). The combined organic solution was washed with brine (50 mL), dried over sodium sulfate, concentrated to afford a residue. The residue was separated by preparative TLC using MeOH/EtOAc (10%) to result in the product (67 mg), as well as a mixture of the product and an impurity (31 mg). $^1$H-NMR (CDCl$_3$) for compound 7 (n=3): δ8.22 (s, 1H, C$_5$H, triazole proton), 7.37 (br, 1H, NH), 7.30-7.13 (m, 9H, Ar—H), 6.77-6.74 (m, 4H, Ar—H), 5.99 (s, 1H), 5.35 (d, J=6.0 Hz, 1H), 4.74 (dd, J=2.1 Hz, J=6.0 Hz, 1H), 4.52 (m, 1H), 3.76 (s, 6H, 2 CH$_3$), 3.64- 3.61 (m, 10H), 3.53-3.47 (m, 2H), 3.30 (s, 3H, CH$_3$), 3.13-3.10 (m, 2H, CH$_2$), 1.55, 1.32 (2s, 6H, 2 CH$_3$). LC-MS: 755.4 (MNa$^+$).

Synthesis of mPEG$_3$-N-Ribavirin 1.0 M HCl in ether (10 mL) was added to a stirred solution of compound 7) (n=3) in methanol (6 mL) at room temperature. The resulting mixture was stirred at room temperature for several hours. The mixture was then concentrated to remove the solvent and HCl. The residue was purified by prep TLC (10% MeOH/DCM) to afford mPEG$_3$-N-Ribavirin. NMR data not available.

Synthesis of mPEG$_5$-N-Ribavirin

NaH (60% dispersion in mineral oil, 1.273 g, 4.039 mmol) was added to a stirred solution of 1-[5'-O-(4,4'-dimethoxytrityl)-2',3'-di-O-isopropylidene-β-D-ribofuranosyl]-1,2,4-triazole-3-carboxamide (compound 6) (778 mg, 1.328 mmol) in anhydrous THF (6 mL) at room temperature. Thereafter, mPEG$_5$-Br (1.273 g, 4.039 mmol) was added. The resulting mixture was stirred at room temperature for 27.5 hours. Saturated NH$_4$Cl (~3 mL) was added to quench the reaction. The solvents were removed under high vacuum. The residue was mixed with a mixture of aq. 5% NaHCO$_3$ solution (40 mL) and DCM (25 mL). The organic phase was separated and the aqueous phase was extracted with DCM (3×25 mL). The combined organic solution was washed with brine, dried over sodium sulfate, concentrated to afford 1.8207 g of crude product.

The crude product was treated with 80% HOAc solution for 23 hours, at 45° C. for 4.5 hours, and then concentrated to remove the solvents. Purification of the crude residue with flash column chromatography on silica gel resulted in mPEG$_5$-N-ribavirin (n=5) (129 mg) ("first lot") and an impure product (503 mg). 40 mL of 1.0 m HCl in ether solution was added to stirred solution of the above impure product in methanol (10 mL) at 0° C. The resulting mixture was stirred at 0° C. for 80 minutes. The solvents and hydrochloride were evaporated under reduced pressure to afford a residue. The residue was purified with reverse phase column chromatography using acetonitrile in water to afford mPEG$_5$-N-ribavirin (90.4 mg) ("second lot") and di-mPEG$_5$-N-ribavirin (compound 17) (128 mg) (See "Example 1D").

$^1$H-NMR (CDCl$_3$) for mPEG$_5$-N-ribavirin (n=5) ("first lot"): 8.51 (s, 1H, C$_5$H, triazole proton), 7.72 (br, 1H, NH), 5.90 (d, J=3.3 Hz, 1H), 4.75 (br, 1H), 4.63 (m, 1H), 4.50 (m, 1H), 4.22 (m, 1H), 4.15 (br, 1H), 3.95-3.76 (m, 3H), 3.63-3.51 (m, 20H), 3.35 (s, 3H, CH$_3$). LC-MS: 479.3 (MH$^+$).

$^1$H-NMR (CDCl$_3$) for mPEG$_5$-N-ribavirin 17 (n=5) ("second lot"): 8.36 (s, 1H, C$_5$H, triazole proton), 5.89 (d, J=2.4 Hz, 1H), 4.57 (m, 2H), 4.35-4.08 (m, 3H), 3.87 (m, 3H), 3.77-3.52 (m, 40H), 3.363 (s, 3H, CH$_3$), 3.357 (s, 3H, CH$_3$). LC-MS: 713.5 (MH$^+$).

Example 1D

Synthesis of Di-mPEG$_n$-N-ribavirin

An exemplary synthetic scheme to prepare Di-mPEG$_n$-N-Ribavirin is schematically shown below.

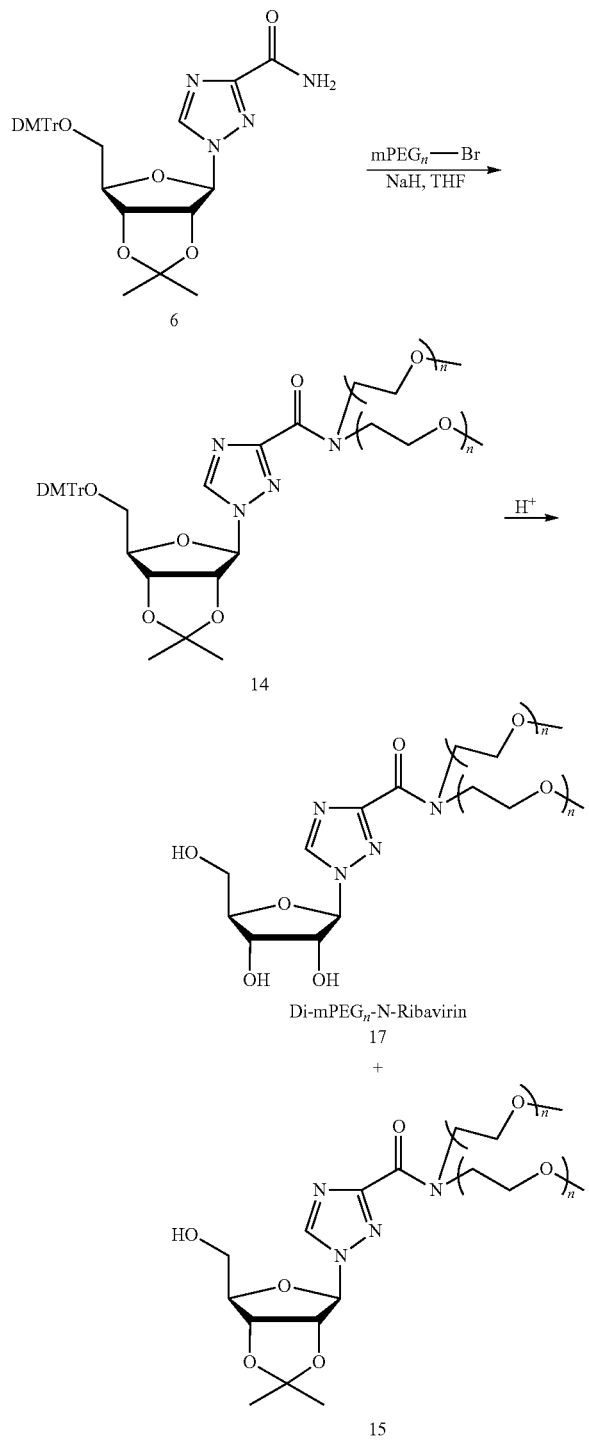

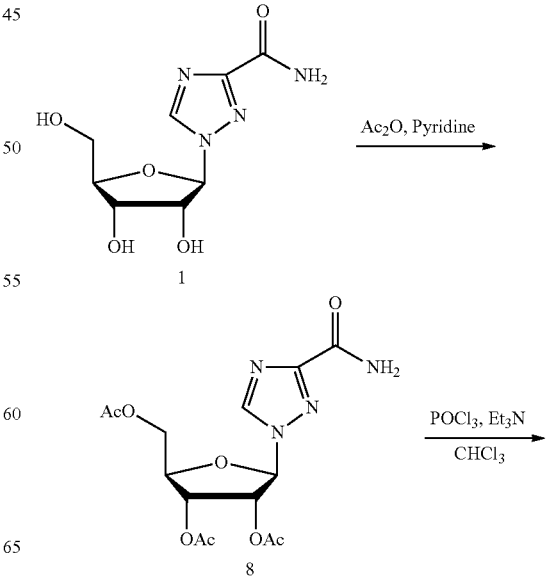

wherein (n) is a variable from between about 1 and about 30 (inclusive).

Synthesis of 1-[5'-O-(4,4'-Dimethoxytrityl)-2',3'-di-O-isopropylidene-β-D-ribofuranosyl]-N-di-mPEG$_3$-1,2,4-triazole-3-carboxamide 14 (n=3)

NaH (60% dispersion in mineral oil, 110 mg, 2.75 mmol) was added to a stirred solution of 1-[5'-O-(4,4'-dimethoxytrityl)-2',3'-di-O-isopropylidene-β-D-ribofuranosyl]-1,2,4-triazole-3-carboxamide (compound 6, made in accordance in Example 1C) (438 mg, 0.747 mmol) in anhydrous THF (5 mL) at room temperature. Then, mPEG$_3$-Br (510 mg, 0.246 mmol) was added. The resulting mixture was stirred at room temperature for 23 hours. Sat NH$_4$Cl (~1 mL) was added to quench the reaction. The solvent was removed under high vacuum. The residue was mixed with a mixture of EtOAc/water (50 mL, 50%). The organic phase was separated and the aqueous phase was extracted with EtOAc (2×25 mL). The combined organic solution was washed with brine, dried over sodium sulfate, concentrated to afford a residue. The residue was separated by flash column chromatography on silica gel using EtOAc/hexane (50-100%) and MeOH/EtOAc (5%, 10%) or MeOH/DCM (0-10%) to result in mono-PEG compound 7 (n=3) (92 mg), di-PEG compound 14 (n=3) (227 mg), de-DMTr group compound 15 (n=3) (33.4 mg) and compound 17 (53 mg). $^1$H-NMR (CDCl$_3$) for compound 14: δ8.22 (s, 1H, C$_5$H, triazole proton), 7.34-7.16 (m, 9H, Ar—H), 6.79-6.75 (m, 4H, Ar—H), 5.98 (s, 1H), 5.19 (dd, J=1.5 Hz, J=6.0 Hz, 1H), 4.73 (ds, J=2.7 Hz, J=6.0 Hz, 1H), 4.46 (m, 1H), 3.76 (s, 6H, 2 CH$_3$), 3.75-3.46 (m, 24H), 3.35 (s, 3H, CH$_3$), 3.34 (s, 3H, CH$_3$), 3.22-3.13 (m, 2H, CH$_2$), 1.55, 1.32 (2s, 6H, 2 CH$_3$). LC-MS: 901.4 (MNa$^+$).

Synthesis of Di-mPEG$_3$-N-ribavirin (17) (n=3)

Following the approach described with respect to the HCl acid treatment of compound 14 to prepare Di-mPEG$_3$-N-ribavirin, compound 17 (n=3) was afforded. No NMR data available.

Synthesis of Di-mPEG$_5$-N-ribavirin (17) (n=5)

Di-mPEG$_5$-N-ribavirin (17) (n=5) was prepared as described in Example 1C.

Example 1D

Preparation of mPEG$_n$-N-ribamidine

An exemplary synthetic scheme to prepare mPEG$_n$-N-Ribamidine is schematically shown below.

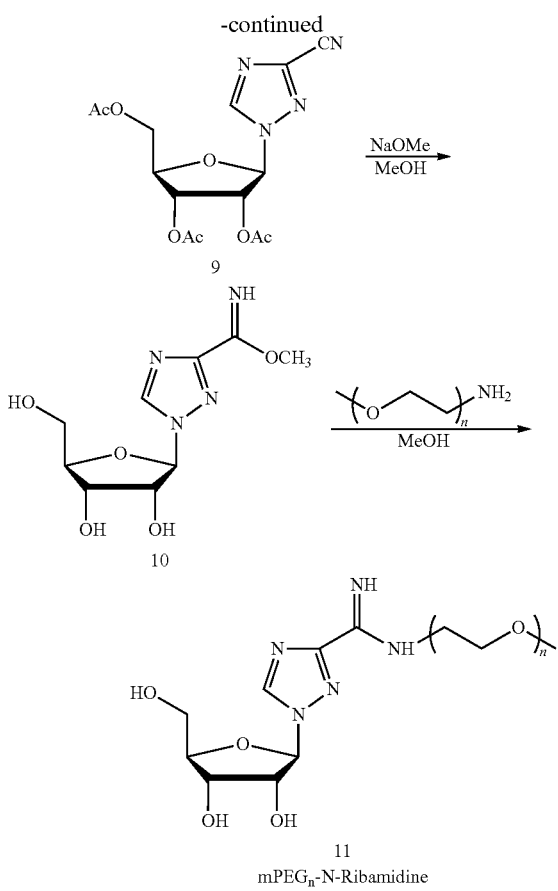

mPEG$_n$-N-Ribamidine wherein (n) is a variable from between about 1 and about 30 (inclusive).

Synthesis of 2',3',5'-O-triacetyl-β-D-ribofuranosyl)-1,2,4-triazole-3-carboxamide 8

A suspension of ribavirin 1 (568 mg, 2.33 mmol) in acetic anhydride (4 mL) and pyridine (1 mL) was stirred at room temperature for 22 hours. The mixture was concentrated under reduced pressure and the residue was dried under high vacuum to afford the product in quantitative yield.

Run 2, a suspension of ribavirin (2.05 g, 8.39 mmol) in acetic anhydride (12 mL) and pyridine (4 mL) was stirred at room temperature for 18 hours. The mixture was concentrated under reduced pressure and the residue was dried under high vacuum to afford the product in quantitative yield.

$^1$H-NMR (DMSO-d$_6$), δ8.84 (s, 1H, C$_5$H, triazole proton), 7.90, 7.71 (2s, 2H, CONH$_2$), 6.32 (d, J=3 Hz, 1H, C$_1$, H), 5.66 (m, 1H), 5.57 (t, J=5.4 Hz, 1H), 4.42-4.37 (m, 2H), 4.10 (m, 1H), 2.10, 2.09, 2.01 (3 s, 9H, COCH$_3$). LC-Ms, 371.2 (MH$^+$).

Synthesis of 3-cyano-2',3',5'-O-triacetyl-β-D-ribofuranosyl)-1,2,4-triazole 9

A mixture of crude 2',3',5'-O-triacetyl-β-D-ribofuranosyl)-1,2,4-triazole-3-carboxamide (compound 8) (934 mg) and triethylamine (5.5 mL) in chloroform (10 mL) was cooled to 0° C. in an ice-water bath. Phosphorus oxychloride (0.7 mL, 7.57 mmol) was added dropwise with stirring and the solution was allowed to warm to room temperature. After the mixture was stirred at room temperature for 17 hours, the brown reaction mixture was concentrated to dryness in vacuum and the residue was dissolved in dichloromethane (20 mL). The organic solution was washed with saturated aqueous sodium bicarbonate (3×60 mL), dried over sodium sulfate, and concentrated. The residue was purified by column chromatography on silica gel using MeOH/DCM (2%) to afford the product (0.718 g, 87% yield based on ribavirin).

Run 2, a mixture of crude 2',3',5'-O-triacetyl-β-D-ribofuranosyl)-1,2,4-triazole-3-carboxamide (from 2.05 g of ribavirin) and triethylamine (20 mL) in chloroform (35 mL) was cooled to 0° C. in an ice-water bath. Phosphorus oxychloride (2.5 mL, 27.04 mmol) was added dropwise with stirring. The solution was stirred at 0° C. for one hour, the ice-water bath was removed and the solution was stirred at room temperature for 17 hours. The brown reaction mixture was concentrated to dryness in vacuum. The residue was purified by column chromatography on silica gel using MeOH/DCM (2%) to afford the product (2.533 g, 86% yield based on ribavirin).

$^1$H-NMR (CDCl$_3$), δ8.36 (s, 1H, C$_5$H, triazole proton), 5.99 (d, J=3.3 Hz, 1H, C$_1$, H), 5.68 (m, 1H), 5.52 (t, J=5.4 Hz, 1H), 4.51-4.41 (m, 2H), 4.24-4.18 (m, 1H), 2.13, 2.12, 2.09 (3 s, 9H, COCH$_3$). LC-Ms, 259.1 [M-C$_3$HN$_4$]$^+$, 375.2 (MNa$^+$).

Synthesis of Methyl 1-β-D-Ribofuranosyl-1,2,4-triazole-3-carboximidate 10

Sodium methoxide (25 wt % solution in methanol, 0.83 mL, 3.63 mmol) was added to a stirred solution of 3-cyano-2',3',5'-O-triacetyl-β-D-ribofuranosyl)-1,2,4-triazole (compound 9) (787 mg, 2.23 mmol) in methanol (15 mL). The mixture was stirred at room temperature for 20 hours. Acetic acid (0.21 mL, 3.70 mmol) was added to quench the reaction. The mixture was concentrated under reduced pressure to afford the crude product. The crude was directly used for the next reaction without purification. $^1$H-NMR (DMSO-d$_6$), δ 8.90 (s, 1H, C$_5$H, triazole proton), 8.82 (bs, 1H, NH), 5.81 (d, J=3.9 Hz, 1H, C$_1$, H), 4.34 (t, J=4.1-4.5 Hz, 1H), 4.13 (t, J=4.8-5.1 Hz, 1H), 3.93 (q, J=4.5-4.8 Hz, 1H), 3.83 (s. 3H, OCH$_3$), 3.64-3.43 (m, 2H) and other sugar protons. LC-Ms, 259.1 (MH$^+$).

Synthesis of mPEG$_n$-ribamidine 11 (n=3)

mPEG$_3$-NH$_2$ (147 mg, 0.90 mmol) was added to a stirred solution of crude methyl amidate 10 (290 mg, ~0.56 mmol)) in methanol (5.0 mL) at room temperature. The resulting mixture was heated at 45° C. for 15 hours. The mixture was cooled to room temperature and concentrated under reduced pressure. The residue was triturated with EtOAc, diluted with ethyl ether, centrifuged. The precipitate was triturated again with DCM, diluted with ethyl ether and centrifuged. The precipitate was collected and dried under high vacuum to afford 156 mg of product. $^1$H-NMR (MeOD) for compound 11 (n=3): 8.81 (s, 1H, C$_5$H, triazole proton), 5.92 (d, J=3.6 Hz, 1H), 4.487 (m, 1H), 4.333 (m, 1H), 4.132 (m, 1H), 3.87-3.53 (m, 19H), 3.358 (s, 3H, CH$_3$). LC-MS: 390.2 (MH$^+$).

Synthesis of mPEG$_n$-ribamidine 11 (n=6)

mPEG$_6$-NH$_2$ (330 mg, 1.12 mmol) was added to a stirred solution of crude methyl amidate 10 (250 mg, ~0.97 mmol)) in methanol (6.0 mL) at room temperature. The resulting mixture was heated at 45° C. for 17 hours. The mixture was cooled to room temperature and concentrated under reduced pressure. The residue was triturated with EtOAc, diluted with ethyl ether, centrifuged. The precipitate was triturated again with DCM, diluted with ethyl ether and centrifuged. The precipitate was collected and dried under high vacuum to afford 126 mg of product. $^1$H-NMR (MeOD) for compound 11 (n=6): 8.59 (s, 1H, C$_5$H, triazole proton), 5.71 (d, J=3.6 Hz, 1H), 4.29 (m, 1H), 4.14 (m, 1H), 3.91 (m, 1H), 3.65-3.31 (m, 31H), 3.15 (s, 3H, CH$_3$). LC-MS: 522.3 (MH$^+$).

Synthesis of mPEG$_n$-ribamidine 11 (n=7)

mPEG$_7$-NH$_2$ (565 mg, 1.66 mmol) was added to a stirred solution of crude methyl amidate 10 (346 mg, ~1.34 mmol)) in methanol (6.0 mL) at room temperature. The resulting mixture was heated at 45° C. for 15.5 hours. The mixture was concentrated under reduced pressure. The residue was triturated with EtOAc, diluted with ethyl ether, centrifuged. The precipitate was triturated again with DCM, diluted with ethyl ether and centrifuged. The precipitate was collected and dried under high vacuum to afford 431 mg of product. $^1$H-NMR (MeOD) for compound 11: 8.61 (s, 1H, C$_5$H, triazole proton), 5.71 (d, J=3.3 Hz, 1H), 4.29 (m, 1H), 4.14 (m, 1H), 3.91 (m, 1H), 3.75-3.33 (m, 35H), 3.15 (s, 3H, CH$_3$). LC-MS: 566.3 (MH$^+$).

Example 2

Antiviral Activity

Ribavirin is a guanosine analogue with broad antiviral activity. The antiviral activities of various compounds prepared in accordance with Example 1 were tested in two in vitro models of viral infection.

Several compounds prepared in accordance with Example 1 were solubilized in DMSO at 40 mM. The compounds were evaluated using a 100 µM high test concentration and serially diluted in half-log increments for the in vitro antiviral assay. Ribavirin (anti-influenza and anti-BVDV) and amantadine (anti-influenza) were purchased from Sigma (St. Louis, Mo.) and used as a positive control compound in the cytoprotection assays.

Anti-Influenza Assay:

Cell Preparation—MDCK cells (female cocker spaniel kidney epithelial; ATCC catalog no. CCL-34) were passaged in T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at 1×10$^5$ cells/mL in tissue culture medium (Dulbecco's Modified Eagles Medium, "DMEM," supplemented with 10% heat inactivated fetal bovine serum, 2 mmol/L L-glutamine, 100 U/mL penicillin, 100 µg/mL streptomycin, 0.1 mM NEAA, and 1 mM sodium pyruvate) to the drug-containing microtiter plates in a volume of 100 µL. The microtiter plates were incubated at 37° C./5% CO$_2$ overnight to allow for cell adherence. Prior to infection, the monolayers were washed three times with Dulbecco's phosphate buffered saline (DPBS).

Virus Preparation—The virus used for the assay was the influenza type A strain A/Hong Kong/8/68. The virus was obtained from ATCC (catalog no. VR-544) and stock virus pools were produced in MDCK cells. A pretitered aliquot of virus was removed from the freezer (−80° C.) and allowed to thaw slowly to room temperature in a biological safety cabinet. Virus was resuspended and diluted into assay medium (DMEM supplemented with 0.5% bovine serum albumin, 2 mmol/L L-glutamine, 100 U/mL penicillin, 100 µg/mL streptomycin, 0.1 mM NEAAZ, 1 mM sodium pyruvate, and 1 µg/mL TPCK-treated trypsin) such that the amount of the virus added to each well in a volume of 100 µL was the amount determined to yield 90 to 95% cell killing at five days post-infection.

Plate Format—each plate contained cell control wells (cells only), virus control wells (cells plus virus), drug toxicity wells (cells plus drug only), drug colorimetric control wells (drug only) as well as experimental wells (drug plus cells plus virus). Samples were tested in triplicate with eleven half-log dilutions per compound.

Anti-Bovine Diarrhea Virus (Surrogate Hepatitis C) Cytopropection Assay:

Cell preparation—MDBK cells (ATCC catalog no CCL-22) were passaged in T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at 1×10$^5$ cells per mL in tissue culture medium (Dulbecco's Modified Eagles Medium, "DMEM," supplemented with 10% horse serum, 2 mmol/L L-glutamine, 100 U/mL penicillin, and 100 µg/mL streptomycin) to the drug-containing microtiter plates in a volume of 100 µL. The microtiter plates were incubated at 37° C./5% CO$_2$ overnight to allow for cell adherence.

Virus Preparation—A pretitered amount of virus was removed from the freezer (−80° C.) and allowed to thaw slowly to room temperature in a biological safety cabinet. Virus was resuspended and diluted into tissue culture medium such that the amount of virus added to each well in a volume of 100 µL was the amount determined to yield 90 to 95% cell killing at five days post infection.

Plate Format—each plate contained cell control wells (cells only), virus control wells (cells plus virus), drug toxicity wells (cells plus drug only), drug colorimetric control wells (drug only) as well as experimental wells (drug plus cells plus virus). Samples were tested in triplicate with eleven half-log dilutions per compound.

Efficacy and Toxicity XTT Used for Influenza and BVDV

Following incubation at 37° C. in a 5% CO$_2$ incubator, the test plates were stained with the tetrazolium dye XTT (2,3-bis(2-methoxy-4-nitro-5-sulfophenyl)-5-[(phenylamino)carbonyl]-2H-tetrazolium hydroxide) purchased from Sigma (St. Louis, Mo., catalog no. X4626). XTT-tetrazolium was metabolized by the mitochondrial enzymes of metabolically active cells to a soluble formazan product, allowing rapid quantitative analysis of the inhibition of virus-induced cell killing. XTT solution was prepared daily as a stock of 1 mg/mL in RPMI1640. Phenazine methosulfate (PMS; Sigma catalog no. P9625) solution was prepared at 0.15 mg/mL in PBS and stored in the dark at −20° C. XTT/PMS stock was prepared immediately before use by adding 40 µL of PMS per mL of XTT solution. Fifty microliters of XTT/PMS was added to each well of the plate and the plate was reincubated for four hours at 37° C. Plates were sealed with adhesive plate sealers shaken gently or inverted several times to mix the soluble formazan product and the plate was read spectrophotometrically at 450/650 nm with a Molecular Devices Vmax plate reader.

Data Analysis—Raw data was collected from the Softmaz Pro software and imported into a Microsoft Excel XLfit4 spreadsheet for analysis by 4 parameter curve fit calculations. Results in the form of EC$_{50}$, TC$_{50}$ and TI are provided in Table 1.

TABLE 1

In vitro Results of Tested Compounds

| Compound | MDCK/Influenza A/Hong Kong/8/68 | | | MDBK/BVDV NADL | | |
|---|---|---|---|---|---|---|
| | $EC_{50}$ (μM) | $TC_{50}$ (μM) | TI | $EC_{50}$ (μM) | $TC_{50}$ (μM) | TI |
| Ribavirin | 16.3 | 79.0 | 4.9 | 5.2 | 61.1 | 12.0 |
| Amantadine | 0.1 | >10.0 | >90.9 | | Not Tested | |
| mPEG$_3$-N-Ribamidine | 67.8 | >100.0 | >1.5 | >100.0 | >100.0 | — |
| mPEG$_6$-N-Ribamidine | >100.0 | >100.0 | — | >100.0 | 87.6 | — |
| mPEG$_7$-N-Ribamidine | >100.0 | >100.0 | — | >100.0 | >100.0 | — |
| mPEG$_5$-N-Ribavirin (two lots) | >100.0 | >100.0 | — | >100.0 | >100.0 | — |
| Di-mPEG$_5$-N-Ribavirin | 5.5 | 19.5 | 3.5 | >100.0 | >100.0 | — |
| Di-mPEG$_7$-N-Ribavirin | >100.0 | >100.0 | — | >100.0 | >100.0 | — |
| Ribavirin | 18.2 | 50.0 | 2.8 | 8.1 | 69.8 | 8.7 |

Infection of MDCK cells with Influenza A virus is cytopathic and resulted in cell death. Treatment of infected cells with ribavirin was cytoprotective with an $EC_{50}$=18.2 μM. Influenza A virus-induced cytotoxicity was also inhibited in the presence of mPEG$_3$-N-ribamidine ($EC_{50}$=67.8 μM). Similarly, di-mPEG$_5$-N-ribavirin was protective against influenza A virus ($EC_{50}$=5.5 μM), although the test molecule was toxic to MDCK cells ($TC_{50}$=19.5 μM). Thus, the therapeutic index (TI) for this molecule is 3.5.

Infection of MDBK cells with Bovine Viral Diarrhea virus (BVDV) is used as a surrogate model for Hepatitis C viral infection. Ribavirin exhibited potent cytoprotection in BVDV-infected cells ($EC_{50}$=8.1 μM), however none of the PEG-conjugates tested was efficacious in this model at concentrations up to 100 μM.

Based on the data obtained, further testing of the conjugates is warranted.

The invention claimed is:

1. A compound having the following structure:

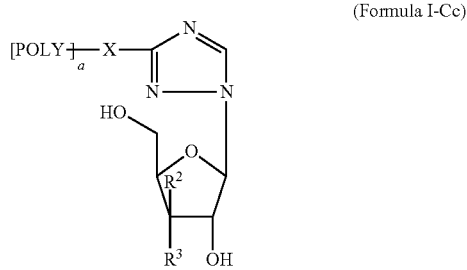

(Formula I-Cc)

wherein:
$R^2$ is hydrogen or hydroxyl;
$R^3$ is hydroxyl when $R^2$ is hydrogen and $R^3$ is hydrogen when $R^2$ is hydroxyl;
(a) is two;
X is an amide linkage; and
each POLY is independently a water-soluble, non-peptidic oligomer, and 5'-phosphates and 3',5'-cyclic phosphates thereof and ammonium and alkali metal salts of each of the 5'-phosphates and 3',5'-cyclic phosphates.

2. The compound of claim 1, wherein the weight average molecular weight of each water-soluble, non-peptidic oligomer is less than 400 Daltons.

3. The compound of claim 1, wherein each water-soluble, non-peptidic oligomer is a poly(alkylene oxide).

4. The compound of claim 3, wherein each poly(alkylene oxide) is a poly(ethylene oxide).

5. The compound of claim 4, wherein the water-soluble, non-peptidic oligomer has a number of repeating monomers in the range of from 1 to 30.

6. The compound of claim 5, wherein the water-soluble, non-peptidic oligomer has a number of repeating monomers in the range of from 1 to 10.

7. The compound of claim 3, wherein the poly(alkylene oxide) includes an alkoxy or hydroxy end-capping moiety.

8. A composition comprising (i) a compound of claim 1, and (ii) a pharmaceutically acceptable excipient.

9. A composition of matter comprising a compound of claim 1 present in a dosage form.

10. The compound of claim 1, wherein the compound is selected from a compound of the formula

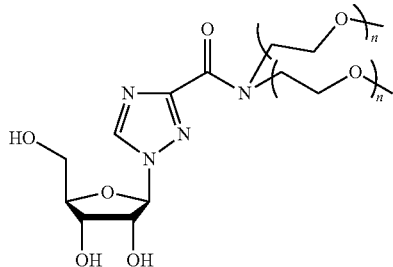

wherein for each occurrence, n is an integer from 1 to 15.

11. The compound of claim 10, wherein for each occurrence, n is an integer from 1 to 10.

12. The compound of claim 11, wherein for each occurrence, n is 5.

13. A composition comprising (i) a compound of claim 10, and (ii) a pharmaceutically acceptable excipient.

* * * * *

UNITED STATES PATENT AND TRADEMARK OFFICE
CERTIFICATE OF CORRECTION

| | | |
|---|---|---|
| PATENT NO. | : 8,466,276 B2 | Page 1 of 1 |
| APPLICATION NO. | : 12/918780 | |
| DATED | : June 18, 2013 | |
| INVENTOR(S) | : Deng et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 260 days.

Signed and Sealed this
Twenty-fourth Day of February, 2015

Michelle K. Lee
*Deputy Director of the United States Patent and Trademark Office*